United States Patent [19]

Weill

[11] Patent Number: 4,596,580

[45] Date of Patent: Jun. 24, 1986

[54] HIP JOINT SOCKET

[75] Inventor: Dan Weill, Vigy, France

[73] Assignee: Protek AG, Bern, Switzerland

[21] Appl. No.: 673,495

[22] Filed: Nov. 20, 1984

[30] Foreign Application Priority Data

Nov. 22, 1983 [DE] Fed. Rep. of Germany ....... 3342035

[51] Int. Cl.$^4$ ................................................. A61F 1/04
[52] U.S. Cl. .................................. 623/22; 128/92 CA; 128/92 C
[58] Field of Search ......................... 3/1.9, 1.91, 1.911, 3/1.912, 1.913; 128/92 C, 92 CA

[56] References Cited

U.S. PATENT DOCUMENTS 4,519,101  5/1985  Schreiber et al. ............. 128/92 CA

FOREIGN PATENT DOCUMENTS 0065482  11/1982  European Pat. Off. ............. 3/1.912

Primary Examiner—Richard J. Apley
Assistant Examiner—David Isabella
Attorney, Agent, or Firm—Toren, McGeady, Stanger, Goldberg & Kiel

[57] ABSTRACT

A hip joint socket includes a plastic socket member and an outer metallic ring member laterally closely enclosing the socket member. The socket member has a conically shaped outer surface in closely fitting engagement with a corresponding conically shaped inner surface on the ring member. Outwardly projecting parts on the socket member fit in a dovetail fashion in corresponding recesses formed in the ring member. The socket is self-fixing within the ring member during any cold flow of its plastic material so that relative movement between the socket member and the ring member is prevented.

11 Claims, 3 Drawing Figures

HIP JOINT SOCKET

BACKGROUND OF THE INVENTION

The present invention is directed to a hip socket joint for cement-free anchoring in the pelvis and it includes a rigid outer member and a socket member secured within the outer member.

In implants in the human body, generally the volume of the foreign member positioned within the tissue of the human body is kept as small as possible. As a result, artificial joint sockets include relatively thin-walled socket members and, due to the sliding characteristics of the socket members frequently made of plastic, particularly polyethylene, the socket members are relatively resilient and transfer the pelvic movements to the sliding surfaces which are in engagement with one another. Such movements lead to the so-called "cherrystone" effect wherein a solid core member works itself out of the softer material during relative movement. Since the socket members are formed of plastics material they tend to experience plastic deformations under continuous stresses and such deformations tend to result in changes in the socket surfaces. Accordingly, the interengagement of the socket surface which forms one of the sliding surfaces of the joint with the other sliding surface formed by the joint head or member is disturbed and leads to increased abrasion.

Therefore, it is a primary requisite that the hip joint socket as a whole is as strong and rigid as possible so that it does not deform during movement of the joint. This requirement has led to a plurality of different sockets in which a socket member is enclosed within and held by an outer member, note German Offenlegungsschrift No. 29 50 536. While this arrangement protects the socket member against the direct influence of pelvic movements, there is the problem, particularly during plastic cold flow of a plastics material socket member, that relative movement takes place between the socket member and its outer member which leads to wear and abrasion between the sliding surfaces. Moreover, a shell-shaped outer member enclosing the socket member represents a large foreign mass within the human body.

SUMMARY OF THE INVENTION

Therefore, it is the primary object of the present invention to provide a rigid conically shaped hip joint socket with a volume which is as small as possible and is resistant to pelvic movements. Further, the socket has the desirable sliding properties of plastics material sockets and during any plastic deformation, the socket member automatically reseats itself.

In accordance with the present invention, the outer member tapers inwardly in the direction away from the socket opening and is formed as an open ring with ribs on its outer circumferential surface and with its inner circumferential surface being conically shaped for receiving the socket member in closely fitting engagement so that there is no relative rotational movement between the ring member and the socket member.

The socket member, generally made of a plastics material, is reinforced by the ring member so that a rigid and strong socket is provided. The annular shape of the outer ring member reduces the foreign body volume in the tissue of the human body and affords a considerable reduction in the socket size as compared to known sockets. In addition, due to the conically shaped interengaging surfaces of the ring member and the socket member, during any flow of the plastics material socket member, the self-fixing action is achieved.

Another significant feature of the invention is the provision of recesses in the face of the ring member generally coplanar with the face of the socket member containing the socket opening. At least three recesses are provided and the sides of the recesses are undercut and outwardly projecting parts on the socket member are similarly shaped so that a dovetail-like interengagement of the parts within the recesses is obtained. The dovetail-shaped parts afford a simple assembly of the socket member in the ring member after the ring member has been implanted into the prepared pelvis by being driven in or screwed in.

The self-fixing action of the socket member after plastic deformation can be facilitated if there is a certain amount of play in the axial direction of the ring member between the bottom of the recesses and the outwardly extending parts on the socket member.

Another advantage involved in the annular or ring-shape of the outer member is that the present invention avoids simultaneous contact between the sides and bottom of the outer member and the socket member which, due to unavoidable tolerances, tends to limit the proper arrangement of the members. There is the problem, if there is contact between the bottoms of the two members, that no clamping effect may be achieved at the side surfaces.

In a simple assembly arrangement, preferably utilizing four outwardly extending dovetail-shaped parts, there is the possibility that during the implantation procedure several socket members with different socket sizes can be inserted on a trial basis into the outer member for selecting the most suitable one.

While the socket member is generally formed of a plastics material, preferably polyethylene, the outer ring member is formed of a metal or a metallic alloy normally employed in implantation procedures, preferably pure titanium is used for the ring member.

For securely anchoring the hip joint socket in the pelvis, the ribs formed on the circumferentially extending outer surface of the ring member are preferably double pitch threads with a slope of 4 to 6 mm, preferably in the range of 4.5 to 5.5 mm, and with a height of 2 to 4 mm, preferably 2.5 to 3.5 mm and the outer surface may be provided with axial cutting grooves so that the threads are self-cutting.

Preferably, the outer shape of the ring member is spherically shaped.

The various features of novelty which characterize the invention are pointed out with particularity in the claims annexed to and forming a part of this disclosure. For a better understanding of the invention, its operating advantages and specific objects attained by its use, reference should be had to the accompanying drawings and descriptive matter in which where are illustrated and described preferred embodiments of the invention.

DETAILED DESCRIPTION OF THE INVENTION

Figure 2:
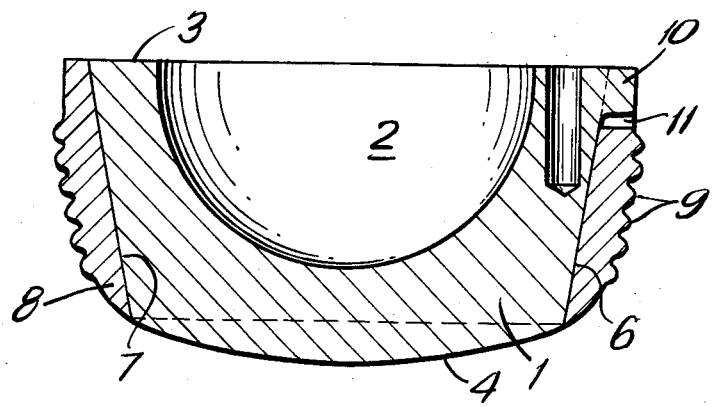
FIG. 2 is a sectional view taken along the line of II—II in FIG. 1.

As illustrated in FIG. 2, the hip joint socket has a cross-section somewhat trapezoidal in appearance, however, the first side 3 of the socket containing the socket opening and the second side or base 4 are not parallel because the base is curved. Generally speaking the socket member 1, as viewed in FIG. 2, has the general form of a truncated cone. Starting from the first side 3 containing the socket opening, the socket 2 is a hollow spherically shaped recess within the socket member 1 and the socket receives the joint head of a femur head prosthesis, not shown.

The socket member 1 has a central axis extending between the first side 3 and the second side or base 4 and the circumferential surface 6 of the socket member is conically shaped tapering inwardly in the direction from the first side 3 toward the second side 4. An outer or ring member 8 laterally encircles the socket member 1 and has a conically shaped inner surface 7 in closely fitting contact with the conically shaped surface 6 on the socket member. The ring member has a first side 12 in generally coplanar relation with the first side 3 of the socket member 1. The second side of the ring member is located in a plane generally parallel with the plane of the first side 3 of the socket member and located between the first side 3 and the second side or base 4. An anchoring surface 9 is formed on the radially outer circumferentially extending surface of the ring member 8 between its first and second sides. The anchoring surface 9 may be in the form of supporting ribs or a screw thread.

The conically shaped surface 6 of the socket member 1 and the radially inner conically shaped surface 7 of the ring member 8 are shaped complementary to one another so they provide a snug or closely fitting interengagement.

Figure 1:
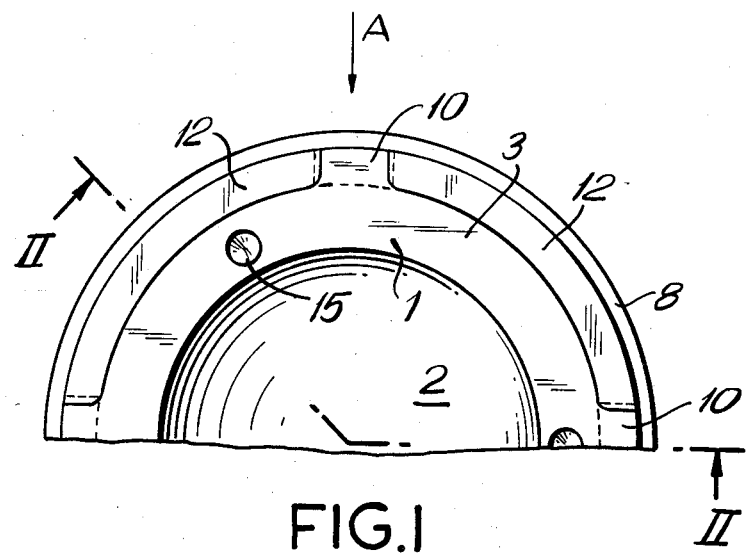
FIG. 1 is a top view of the maximum transverse plane of the hip joint socket of the present invention with the plane extending transversely of the axis of the conically shaped surfaces in the socket.

As shown in the half plan view of the socket member in FIG. 1, the socket member 1 at the first side 3 has four outwardly extending parts 10 equiangularly spaced apart at 90° from one another and these parts snap into correspondingly shaped recesses 11 extending inwardly from the first side 12 of the ring member 8. As can be noted in FIG. 3, the side surfaces of the parts 10, that is the surfaces extending in the direction between the first and second sides 3, 4 have a dovetail-shape and the corresponding sides of the 14 of the recesses are undercut, that is, the sides 14 are in diverging relationship in the direction from the first side 3 to the second side 4 of the socket member. With the parts 10 secured within the recesses 11, the socket member is securely retained within the ring member 8 so that it cannot be displaced or moved relative to the ring member.

Figure 3:
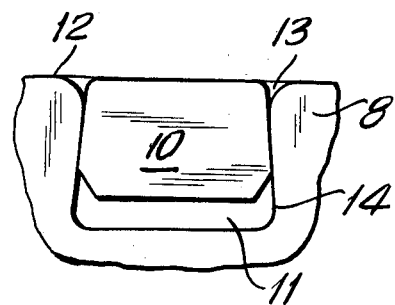
FIG. 3 is an enlarged partial view of FIG. 1 taken in the direction of the arrow A in FIG. 1.

As can be seen in FIGS. 2 and 3, while the upper surface of the parts 10 are located generally in the plane of the first side 3, the lower sides of the parts 10 are spaced upwardly from the base of the recesses so that there is a certain amount of play within the recesses for the parts 10 in the central axis direction of the socket member 1. By sizing the parts 10 so that their height in the central axis direction is less than the depth of the recesses 11, a certain amount of play is provided so that the socket member can move more deeply into the ring member with the conically shaped surface 6 moving relative to the conically shaped surface 7 on the ring member during plastic deformation without any deformation taking place at the parts 10 within the recesses 11.

Three angularly spaced bores 15 are formed in the socket member 1 extending inwardly from the first side 3 so that an instrument or tool can be inserted into the socket member.

While specific embodiments of the invention have been shown and described in detail to illustrate the application of the inventive principles, it will be understood that the invention may be embodied otherwise without departing from such principles.

I claim:

1. A hip joint socket for cement-free anchoring in the pelvis, comprising a rigid outer member, and a socket member secured within said outer member, said outer member and said socket member each having a central axis and a first side and a second side extending transversely of the central axis with said first and second sides of each being disposed in spaced relation relative to the central axis, said first sides of said outer member and socket member being disposed in approximately the same plane and said socket member forming a socket therein having an opening located in the plane containing said first side of said socket member, said outer member being ring-shaped with a radially outer surface and a radially inner surface both extending around the central axis and between the first and second sides thereof, said outer surface tapering inwardly in the direction from the first side toward said second side, ribs formed in said outer surface extending transversely of the central axis of said outer member, said inner surface being conically shaped and tapering inwardly in the direction from the first side toward the second side, said socket member having an outer surface extending between said first and second sides thereof with said socket member outer surface being conically shaped and tapering inwardly in the direction from the first side toward the second side of said socket member, wherein the improvement comprises that at least three recesses are formed in said inner surface of said ring member, said recesses being a dove tail shape groove extending radially and substantially in a direction of the longitudinal axis of said socket, and wherein said socket member having a complementary outwardly extending ribs formed on said outer surface thereof so that said socket member is fitted in said outer member so that said socket member cannot rotate relative to said outer member.

2. A hip joint socket, as set forth in claim 1, wherein said outwardly extending ribs have a dimension in the direction between the first and second sides of said socket member less than the corresponding dimension of said recesses extending inwardly from the side of said outer member, leaving play in the axial direction.

3. A hip joint socket, as set forth in claim 1 or 2, wherein four recesses are formed in said ring member.

4. A hip joint socket, as set forth in claim 1 or 2, wherein said ring member is formed of pure titanium and said socket member is formed of polyethylene.

5. A hip joint socket, as set forth in claim 1 or 2, wherein said radially outer surface of said outer member is spherically shaped.

6. A hip joint socket, as set forth in claim 1 or 2, wherein said ribs on the outer surface of said outer member are constructed as double pitch threads.

7. A hip joint socket, as set forth in claim 6, wherein said threads have a slope of 4 to 6 mm.

8. A hip joint socket, as set forth in claim 7, wherein said threads have a slope of 4.5 to 5.5 mm.

9. A hip joint socket, as set forth in claim 7, wherein said threads have a height in the range of 2 to 4 mm.

10. A hip joint socket, as set forth in claim 9, wherein said threads have a height in the range of 2.5 to 3.5 mm.

11. A hip joint socket, as set forth in claim 6, wherein said double pitch thread is provided with axially cutting grooves.

* * * * *